(12) United States Patent
Lee et al.

(10) Patent No.: US 8,387,619 B2
(45) Date of Patent: Mar. 5, 2013

(54) RESPIRATORY MASK

(75) Inventors: Gary C. J. Lee, I-Lan (TW); Shu-Ping Zou, Shihlin Dist (TW); Yi-He Lee, Shihlin Dist (TW)

(73) Assignee: Galemed Corporation, Wu-Jia, I-Lan (TW)

( * ) Notice: Subject to any disclaimer, the term of this patent is extended or adjusted under 35 U.S.C. 154(b) by 794 days.

(21) Appl. No.: 12/535,166

(22) Filed: Aug. 4, 2009

(65) Prior Publication Data

US 2010/0031963 A1 Feb. 11, 2010

(30) Foreign Application Priority Data

Aug. 5, 2008 (TW) .............................. 97213963 U

(51) Int. Cl.
*A62B 18/02* (2006.01)
*A62B 18/08* (2006.01)
(52) U.S. Cl. ............................... 128/206.21; 128/207.11
(58) Field of Classification Search ............. 128/205.25, 128/206.21–206.28, 207.11–207.13
See application file for complete search history.

(56) References Cited

U.S. PATENT DOCUMENTS

| | | | | |
|---|---|---|---|---|
| 7,047,971 B2* | 5/2006 | Ho et al. | | 128/207.11 |
| 7,069,932 B2* | 7/2006 | Eaton et al. | | 128/206.24 |
| 7,225,811 B2* | 6/2007 | Ruiz et al. | | 128/207.11 |
| 7,287,528 B2* | 10/2007 | Ho et al. | | 128/206.21 |
| 7,455,063 B2* | 11/2008 | Geiselhart et al. | | 128/205.25 |
| 7,472,703 B2* | 1/2009 | Hernandez et al. | | 128/206.21 |
| 7,631,644 B2* | 12/2009 | Ho et al. | | 128/206.21 |
| 2003/0196658 A1* | 10/2003 | Ging et al. | | 128/201.22 |
| 2004/0025883 A1* | 2/2004 | Eaton et al. | | 128/206.27 |
| 2006/0249157 A1* | 11/2006 | Eaton et al. | | 128/206.24 |
| 2006/0249159 A1* | 11/2006 | Ho et al. | | 128/207.13 |
| 2007/0221226 A1* | 9/2007 | Hansen et al. | | 128/206.21 |
| 2008/0035152 A1* | 2/2008 | Ho et al. | | 128/206.26 |
| 2008/0210241 A1* | 9/2008 | Schulz et al. | | 128/206.21 |
| 2009/0032025 A1* | 2/2009 | Geiselhart et al. | | 128/206.24 |
| 2009/0107506 A1* | 4/2009 | Collazo et al. | | 128/206.21 |
| 2010/0031963 A1* | 2/2010 | Lee et al. | | 128/207.11 |
| 2010/0065060 A1* | 3/2010 | Ho et al. | | 128/206.26 |
| 2011/0126838 A1* | 6/2011 | Alberici et al. | | 128/207.11 |
| 2011/0297158 A1* | 12/2011 | Austin et al. | | 128/206.28 |

\* cited by examiner

*Primary Examiner* — Loan Thanh
*Assistant Examiner* — Sandhara Ganesan
(74) *Attorney, Agent, or Firm* — Merchant & Gould P.C.

(57) ABSTRACT

A respiratory mask includes a single-piece first cushion ring defining an airflow channel and having a front cover-engaging end portion and a rear abutment end portion adapted to abut against a user's face below the forehead, a cover shell having a cover plate engaged to the front cover-engaging end portion and provided with a connecting hole that is adapted to be connected to an air supply source, a resilient forehead support connected to a top end of the front cover-engaging end portion and bendable toward the rear abutment end portion, a resilient forehead abutment body connected to a top end of and supported by the resilient forehead support and including a second cushion ring adapted to abut against the forehead of the user, and an adjustable head strap unit connected to the first cover shell and the resilient forehead abutment body.

18 Claims, 9 Drawing Sheets

RESPIRATORY MASK

CROSS-REFERENCE TO RELATED APPLICATION

This application claims priority of Taiwanese Application No. 097213963, filed on Aug. 5, 2008.

BACKGROUND OF THE INVENTION

1. Field of the Invention

This invention relates to a respiratory mask, more particularly to a respiratory mask for a continuous positive airway pressure (CPAP) machine.

2. Description of the Related Art

An effective way of treating obstructive sleep apnea is to use a continuous positive airway pressure (CPAP) machine. A person suffering from obstructive sleep apnea wears a respiratory mask that is connected to a pump of the machine during his/her sleep. The pump is controlled by a pressure adjustment main unit to continuously pump air into the user's airway to produce a continuous positive airflow, so that the user's airway may remain open and unblocked.

Referring to FIG. 1, a currently available respiratory mask 9 for a CPAP machine is shown to include a mask body 91, a forehead support 93, a forehead pad 94, and a head strap 95. The mask body 91 has a cushion pad 911 covering the user's nose and mouth, and a connecting hole 912 connected fluidly to an air supply tube 92. The air supply tube 92 is connected to a pump (not shown) for supply of a continuous positive pressure airflow into the mask 9. The mask body 91 further has left and right lug portions 913 (only one is visible) projecting respectively from left and right sides thereof and provided respectively with lower positioning holes 9131 (only one is visible). The forehead pad 94 is connected to a top end of the mask body 91 through the forehead support 93, and has two opposite upper positioning holes 941 (only one is visible). Four end portions 951 (only two are visible) of the head strap 95 are inserted respectively through the upper and lower positioning holes 941, 9131, and are then folded back to fix upon themselves through the use of hook and loop fasteners. In this state, the mask body 91 covers tightly the user's nose and mouth, and the forehead pad 94 abuts against the user's forehead. Hence, the pressure of wearing the mask 9 is distributed to the user's forehead and around the users nose and mouth to minimize discomfort during use of the mask 9.

However, due to the different facial dimensions of users, and due to the fact that the forehead support 93 is hard and is not adjustable, in some instances, the cushion pad 911 and the forehead pad 94 do not simultaneously and respectively abut against the user's forehead and the user's nose and mouth, so that the pressure cannot be effectively distributed to the user's forehead and the user's nose and mouth. Further, since the four end portions 951 of the head strap 95 must extend through the respective upper and lower positioning holes 941, 9131 and be folded back to fix upon themselves, the fixing operation of the head strap 95 is troublesome and cannot be quickly accomplished. In a case where the user must get up in the middle of the night to go to the toilet, the light must be switched on in order to remove the mask 9 and put it on again. This is not only troublesome, but may make it difficult for the user to fall back to sleep.

SUMMARY OF THE INVENTION

Therefore, the object of the present invention is to provide a respiratory mask that is capable of overcoming the aforementioned drawbacks of the prior art.

According to this invention, a respiratory mask comprises a single-piece first cushion ring, a cover shell, a resilient forehead support, a resilient forehead abutment body, and an adjustable head strap unit. The single-piece first cushion ring defines an airflow channel, and has a surrounding wall that extends around the airflow channel and that includes a rear abutment end portion adapted to abut against a user's face below the forehead, and a front cover-engaging end portion opposite to the rear abutment end portion. The cover shell has a cover plate engaged to the front cover-engaging end portion and provided with a connecting hole that is adapted to be connected to an air supply source. The resilient forehead support is connected to a top end of the front cover-engaging end portion, and is bendable toward the rear abutment end portion. The resilient forehead abutment body is connected to a top end of and supported by the resilient forehead support, and includes a second cushion ring adapted to abut against the forehead of the user. The adjustable head strap unit is connected to the first cover shell and the resilient forehead abutment body.

BRIEF DESCRIPTION OF THE DRAWINGS

Other features and advantages of the present invention will become apparent in the following detailed description of the preferred embodiment of the invention, with reference to the accompanying drawings, in which.

DETAILED DESCRIPTION OF THE PREFERRED EMBODIMENT

Figure 1:
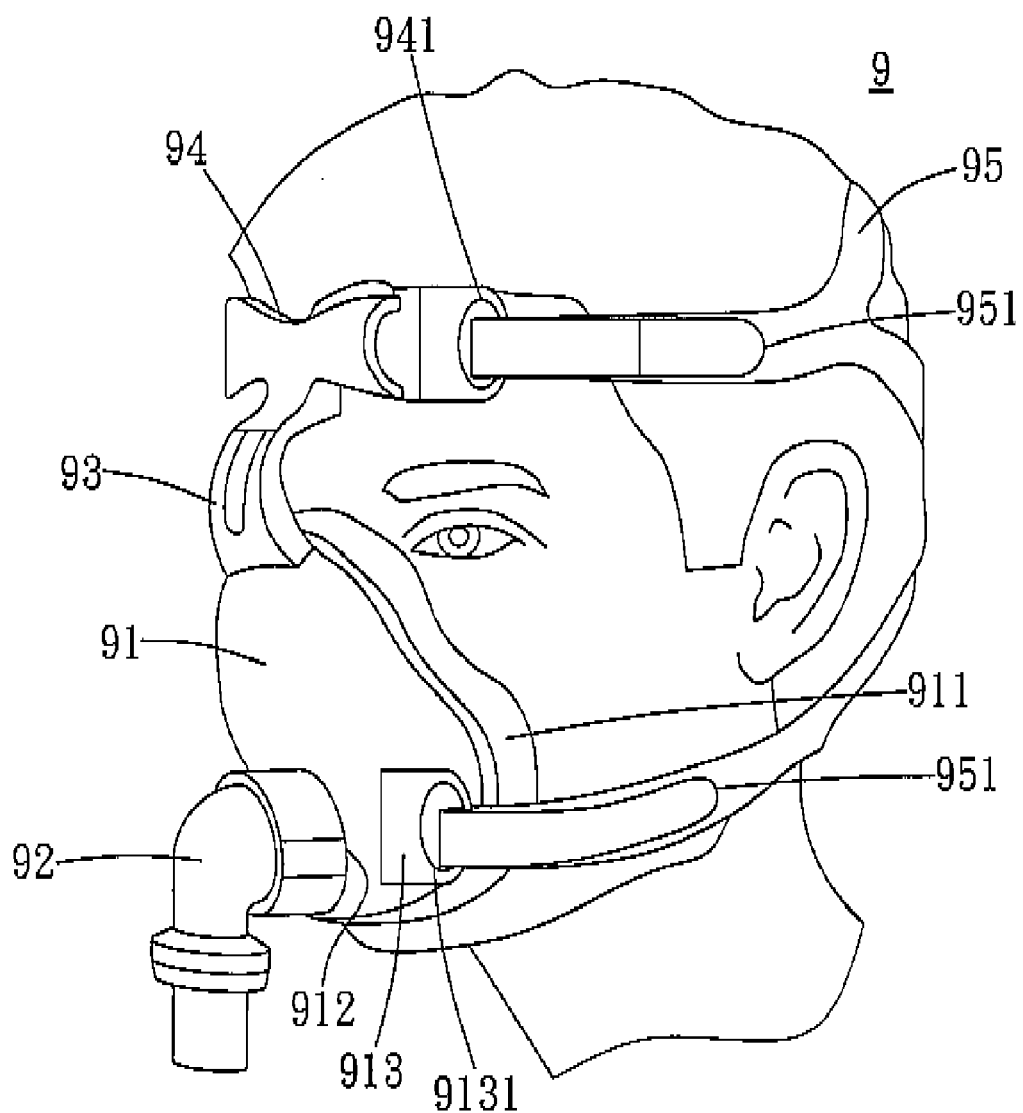
FIG. 1 is a perspective view of a conventional respiratory mask in a state of use.

Referring to FIGS. 2 to 10, a respiratory mask 100 according to the preferred embodiment of the present invention is shown to comprise a mask body 1, a resilient forehead support 2, a resilient forehead abutment body 3, and an adjustable head strap unit 4.

The mask body 1 is adapted to cover a user's face around the nose and mouth. Alternatively, the mask body 1 may be adapted to cover the user's nose only by varying the size of the entire mask body 1. The mask body 1 includes a single-piece first cushion ring 11, a first cover shell 12, a first clamping ring 13, and an air supply tube 14.

Figure 5:
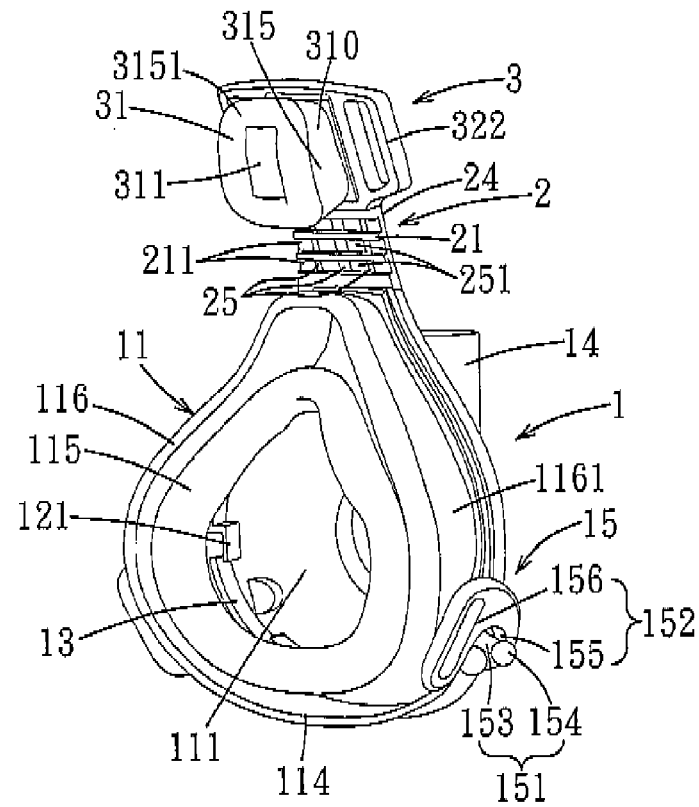
FIG. 5 is an assembled rear perspective view of FIG. 3.
Figure 6:
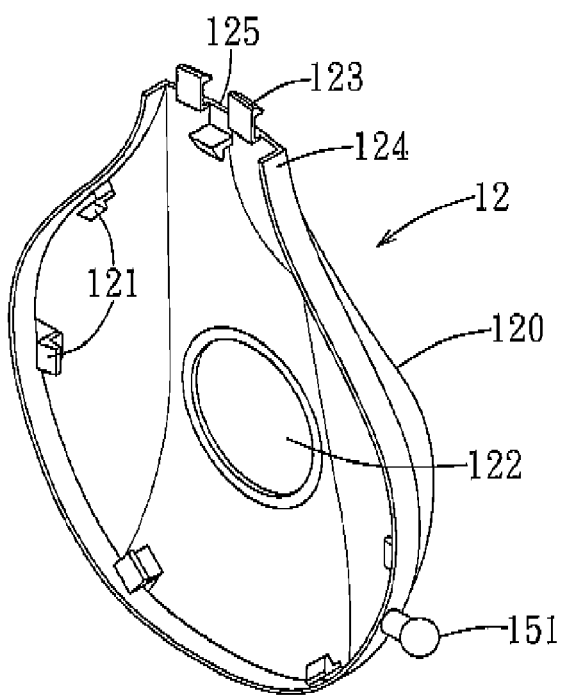
FIG. 6 is a schematic front view of a first cover shell of the preferred embodiment.
Figure 7:
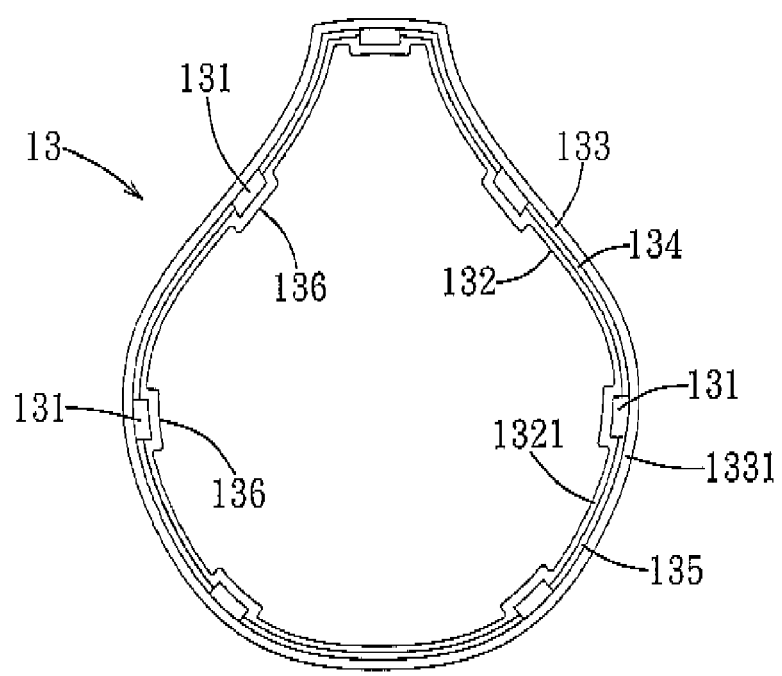
FIG. 7 is a schematic front view of a first clamping ring of the preferred embodiment.
Figure 8:
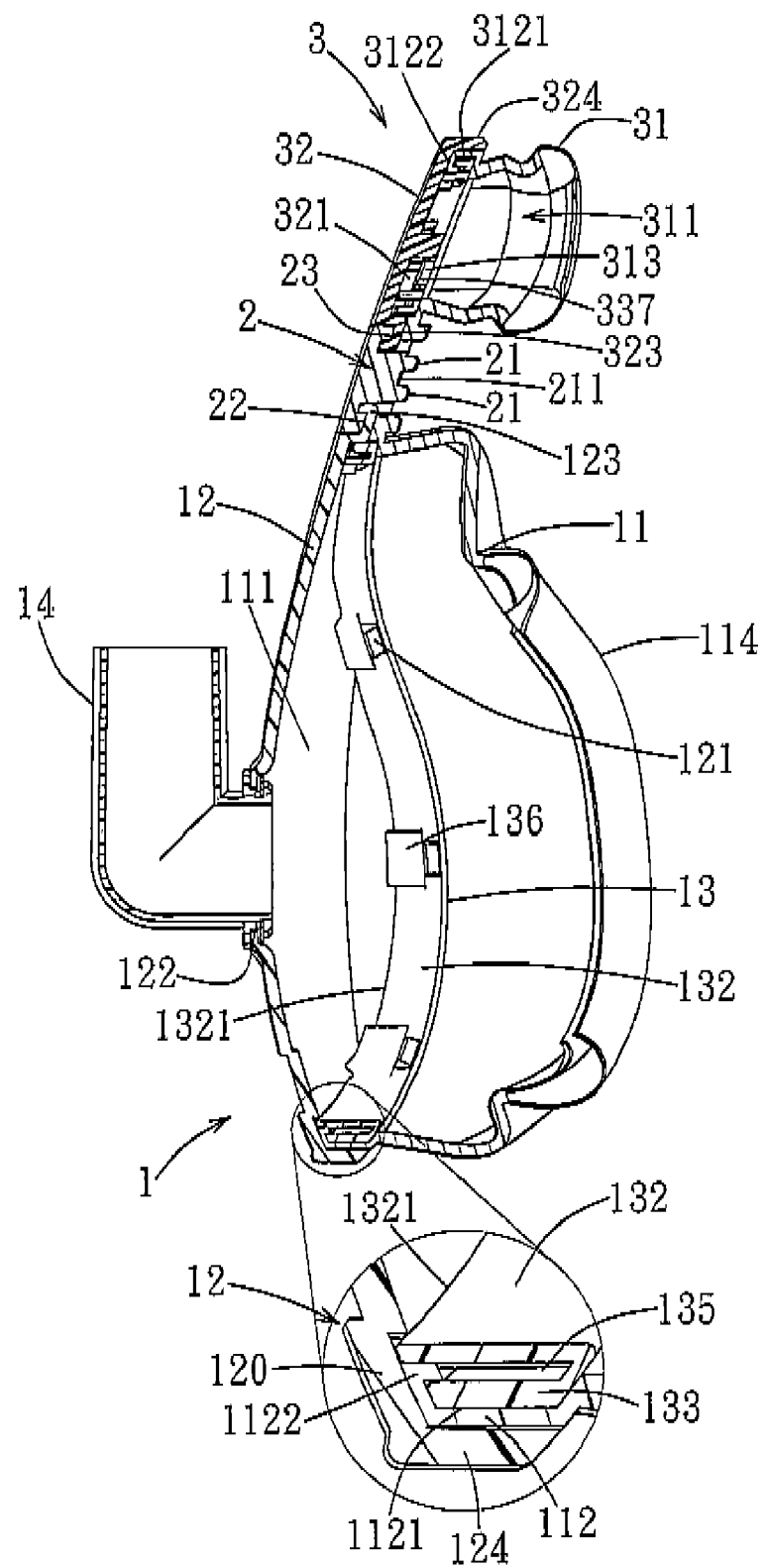
FIG. 8 is a sectional side view of the preferred embodiment taken along line VI-VI of FIG. 4.
Figure 9:
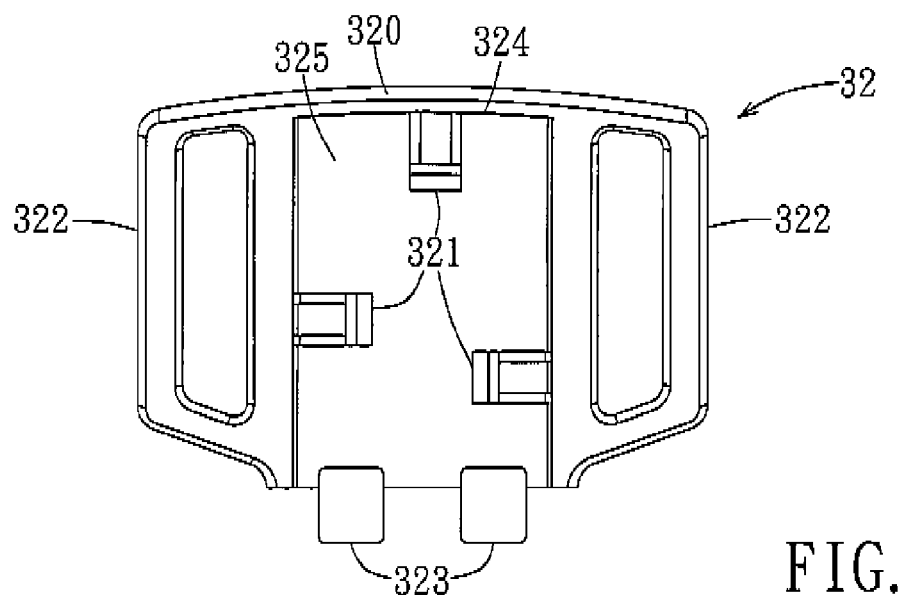
FIG. 9 is a schematic rear view of a second cover shell of the preferred embodiment.
Figure 10:
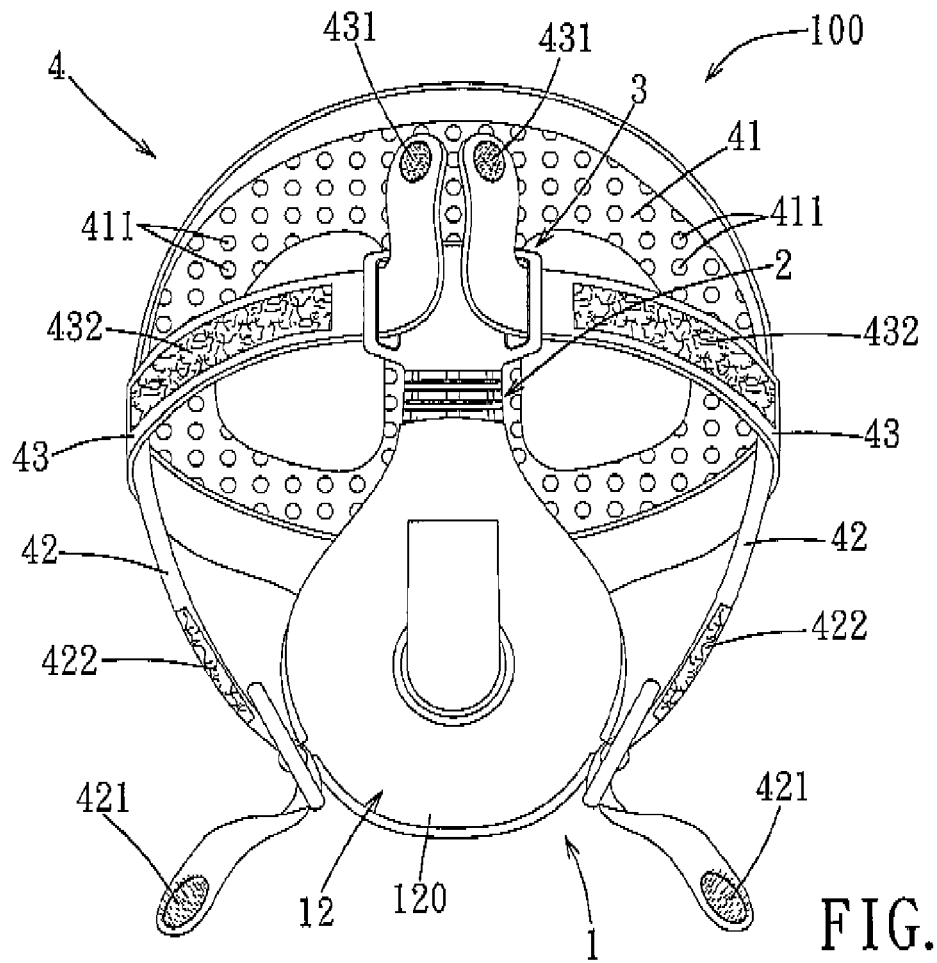
FIG. 10 is a schematic front view of the preferred embodiment.

The single-piece first cushion ring 11 may be made of silicone or other materials capable of providing a cushioning effect, defines an airflow channel 111, and has a first surrounding wall 110 that extends around the airflow channel 111 and that includes a first rear abutment end portion 114 adapted to abut against the user's face below the forehead, i.e., against the user's nose and mouth, and a first front cover-engaging end portion 112 opposite to the first rear abutment end portion 114. The first front cover-engaging end portion 112 has an inner surface provided with an annular first retaining recess 1121 extending around the airflow channel 111, an annular first end flange 1122 projecting inwardly from an end of the first front cover-engaging end portion 112 in proximity to the first retaining recess 1121, and a plurality of angularly spaced-apart positioning grooves 113 formed in the annular first end flange 1122. The first rear abutment end portion 114, as shown in FIG. 5, includes a first annular contact face 116 adapted to contact the user's face, a first annular wall 1161 extending forwardly from an outer peripheral end of the first annular contact face 116 toward the first front cover-engaging end portion 112, a second annular contact face 115 surrounded by the first annular contact face 116 and adapted also to contact the user's face, and a second annular wall 1151 (see FIG. 3) extending around the airflow channel 111, extending forwardly from an outer peripheral end of the second annular contact face 115 toward the first front cover-engaging end portion 112, and surrounded by the first annular wall 1161. The first and second annular walls 1161, 1151 are interconnected in proximity to the first front cover-engaging end portion 112. The second annular contact face 115 is softer than the first annular contact face 116. Through the presence of the first and second annular contact faces 116, 115, the mask body 1 of the present invention can accommodate different kinds of curves on the user's face, so that a sealing effect of the entire mask body 1 can be enhanced.

The first cover shell 12 has a first cover plate 120 formed with a connecting hole 122 that communicates fluidly with the airflow channel 111, and a first cover flange 124 projecting rearwardly from a peripheral end of the first cover plate 120. The first cover plate 120 has a non-flanged top end 125 provided with a pair of upper engaging hooks 123 that project upwardly therefrom. The first cover shell 12 may be made of polycarbonate (PC) or other plastic materials that are strong. Moreover, the first cover shell 12 may be provided with a feeding hole and a cover covering the same in a conventional manner, so that the user may eat while wearing the respiratory mask 100 by passing food through the feeding hole. Further, the first cover shell 12 may also be provided with a detection hole in a known manner for receiving a sensing end of a carbon dioxide measuring apparatus.

The air supply tube 14 has one end 141 inserted into the connecting hole 122 to communicate fluidly with the airflow channel 111 and fixed to the first cover plate 120 through a positioning ring 141. The other end 142 of the air supply tube 14 is adapted to be connected to a pump (not shown) for supply of a continuous airflow.

The first clamping ring 13 is fitted in the annular first retaining recess 1121, and has an inner peripheral wall 132 that extends around the airflow channel 111 and that has front and rear edges 1321, 1322, and a plurality of angularly spaced-apart hole-forming portions 136 projecting inwardly from the inner peripheral wall 132. The first clamping ring 13 further has an outer peripheral wall 133 that extends around the inner peripheral wall 132, that abuts against the inner surface of the first front cover-engaging end portion 112, and that has front and rear edges 1331, 1332, and an annular groove 135 formed between the inner and outer peripheral walls 132, 133 and opening at the front edges 1321, 1331 of the inner and outer peripheral walls 132, 133. A web portion 134 interconnects the rear edges 1322, 1332 of the inner and outer peripheral walls 132, 133. The front edge 1331 of the outer peripheral wall 133 abuts against the annular first end flange 1122.

A plurality of first interlocking units are provided on the first cover plate 120 and the first clamping ring 13 so as to interlock the first cover shell 12 and the first cushion ring 11, so that the first cover shell 12 covers one end of the airflow channel 111. The first interlocking units include a plurality of angularly spaced-apart first engaging holes 131 provided in the first clamping ring 13, and a plurality of angularly spaced-apart first engaging hooks 121 (see FIG. 6) provided on the first cover plate 120 to engage respectively the first engaging holes 131. The first engaging holes 131 are defined respectively by the hole-forming portions 136, extend through the web portion 134, and communicate spatially with the annular groove 135. The first engaging hooks 121 project rearwardly from an inner surface of the first cover plate 120, extend through the respective positioning grooves 133 into the respective first engaging holes 131, and are spaced apart from the first cover flange 124.

The first cover flange 124 extends over and abuts against an outer surface of the first front cover-engaging end portion 112 in proximity to the first end flange 1122. The front edge 1331 of the outer peripheral wall 133 clamps the first end flange 1122 against the inner surface of the first cover plate 120 in proximity to the first cover flange 124. The annular groove 135 receives an inner end of the first end flange 1122. The first cover flange 124 and the outer peripheral wall 133 clamp therebetween the first front cover-engaging end portion 112 in proximity to the first end flange 1122. Through such connections, the first cover shell 12 is connected sealingly to the first front cover-engaging end portion 112 of the mask body 1.

Figure 3:
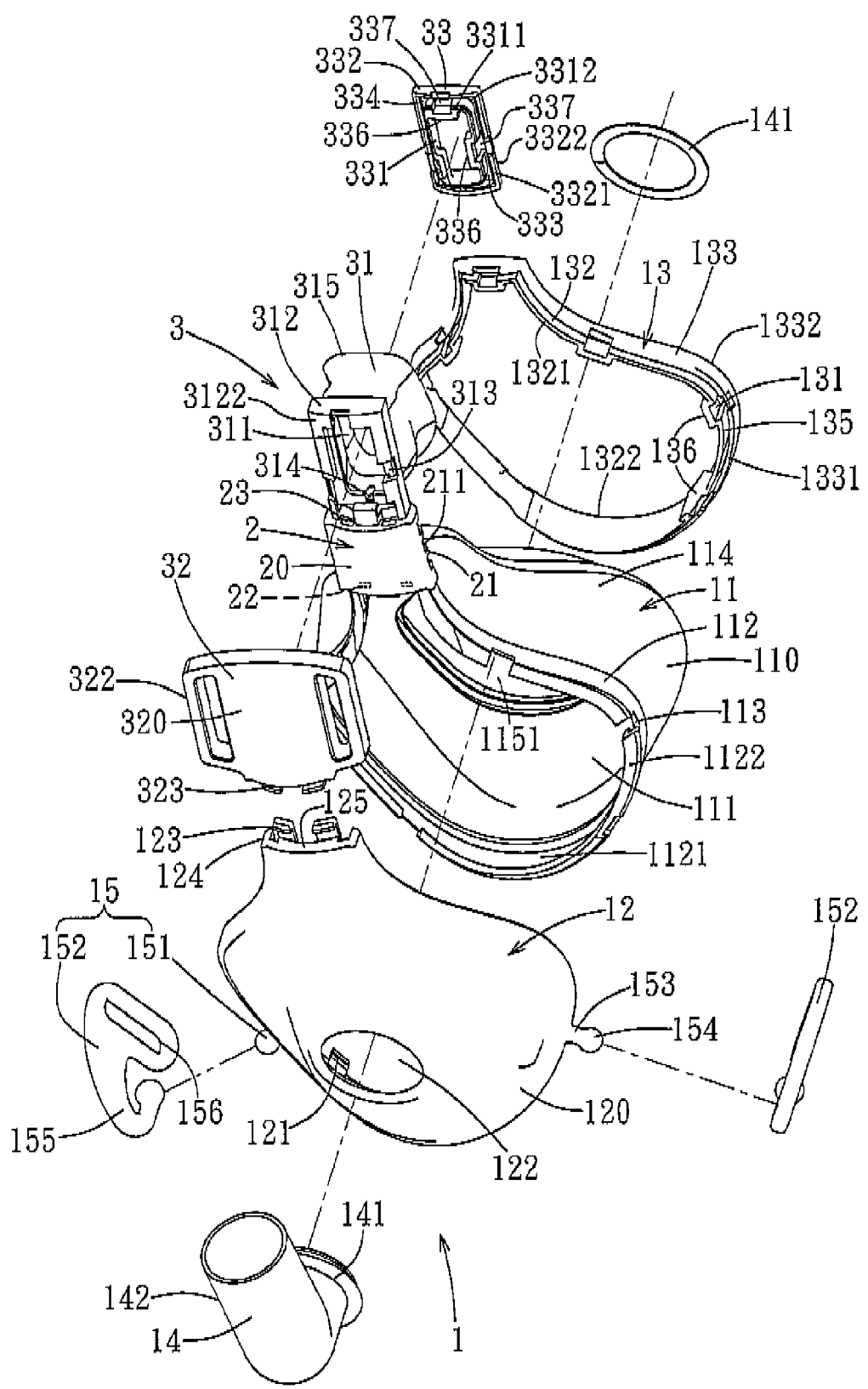
FIG. 3 is an exploded perspective view of the preferred embodiment, but without an adjustable head strap unit.
Figure 4:
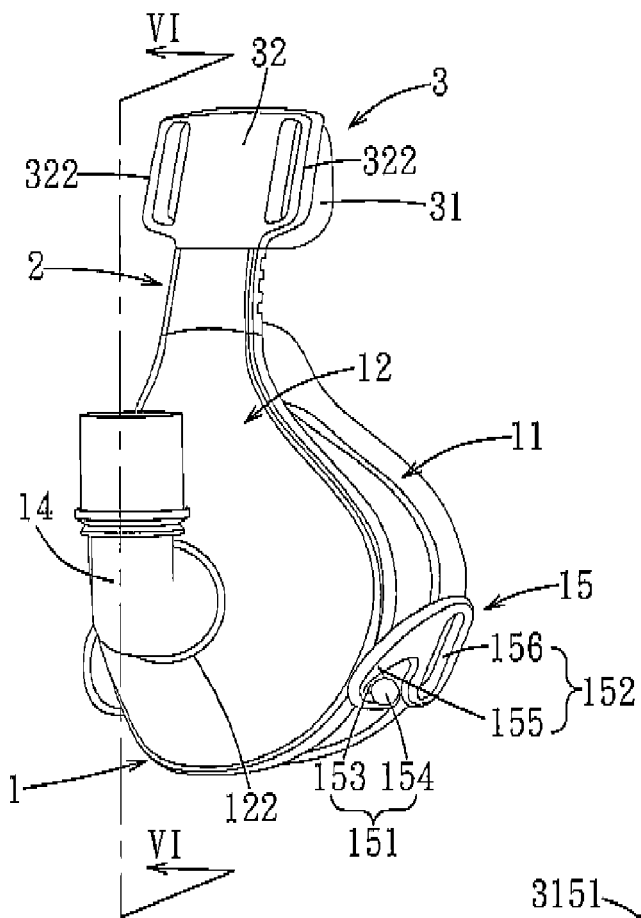
FIG. 4 is an assembled front perspective view of FIG. 3.

With reference to FIGS. 3 and 5, the resilient forehead support 2 is made of silicone, but is not limited thereto. The forehead support 2 has a main body 20 connected to a top end of the first front cover-engaging end portion 112 and bendable toward the first rear abutment end portion. The main body 20 includes a front planar wall 24, a plurality of substantially horizontal ribs 21 projecting rearwardly from the front planar wall 24, horizontal valleys 211 between the horizontal ribs 21, a plurality of vertical ribs 25 disposed between the front planar wall 24 and the horizontal ribs 21, vertical valleys 251 formed between the vertical ribs 25, a pair of lower engaging grooves 22 formed in a bottom end of the main body 20, and a pair of upper engaging grooves 23 formed in a top end of the main body 20. The upper engaging hooks 123 of the first cover plate 120 are engaged respectively to the lower engaging grooves 22. Preferably, the upper engaging hooks 123 are made of a flexible material for bearing the stress created when the forehead support 2 is bent resiliently toward the user. The positions of the upper engaging hooks 123 and the lower engaging grooves 22 may be interchanged, and the numbers thereof may be increased as needed.

The resilient forehead abutment body 3 is connected to and is disposed above the forehead support 2 so that the forehead abutment body 3 is supported by the forehead support 2, and includes a second cushion ring 31, a second cover shell 32, and a second clamping ring 33. The second cushion ring 31 is made of silicone in this embodiment. Alternatively, the second cushion ring 31 may be made of other materials capable of providing a cushioning effect. The second cushion ring 31 defines a passage 311, and has a second surrounding wall 310 that extends around the passage 311 and that has a second rear abutment end portion 315 and a second front cover-engaging end portion 312. The second rear abutment end portion 315 has an annular contact face 3151 adapted to abut against the user's forehead and that is softer than the other parts of the second surrounding wall 310. The second front cover-engaging end portion 312 is connected integrally to the top end of the main body 20 of the forehead support 2, and has a construction similar to that of the first front cover-engaging end portion 112, but is smaller in size. Particularly, the second front cover-engaging end portion 312 has an inner surface provided with an annular second retaining recess 3121 (see FIG. 8) extending around the passage 311, an annular second end flange 3122 projecting inwardly from an end of the second cover-engaging end portion 312 in proximity to the annular second retaining recess 3121, and a plurality of spaced-apart positioning grooves 313 formed in the second end flange 3122. A vent hole 314 is provided between the second rear abutment end portion 315 and the second front cover-engaging end portion 312, and communicates fluidly with the passage 311. In this embodiment, the resilient forehead support 2, the first cushion ring 11, and the second cushion ring 31 are connected integrally to form one body, and the forehead support 2 is configured as a neck portion between the first cushion ring 11 and the forehead abutment body 3.

The second cover shell 32 has a second cover plate 320 provided with an indentation 325 that is defined by an inner peripheral wall 324, left and right strap-engaging looped portions 322 provided respectively on left and right sides of the second cover plate 320, and a pair of lower engaging hooks 323 projecting downwardly from a bottom end of the second cover plate 320 and engaged respectively to the upper engaging grooves 23. The inner peripheral wall 324 extends over and abuts against an outer surface of the second front cover-engaging end portion 312 in proximity to the second end flange 3122.

The second clamping ring 33 has a construction similar to that of the first clamping ring 13, but is smaller in size and has a rectangular cross section. The second clamping ring 33 is fitted in the second retaining recess 3121, and has an inner peripheral wall 331 that extends around the passage 311 and having front and rear edges 3311, 3312, a plurality of angularly spaced-apart hole-forming portions 336 projecting inwardly from the inner peripheral wall 331, an outer peripheral wall 332 that extends around the inner peripheral wall 331 and that has front and rear edges 3321, 3322, an annular groove 334 formed between the inner and outer peripheral walls 331, 332 and opening at the front edges 3311, 3321 of the inner and outer peripheral walls 331, 332, and a web portion 333 interconnecting rear edges 3312, 3322 of the inner and outer peripheral walls 331, 332. The front edge 3321 of the outer peripheral wall 332 clamps the second end flange 3122 against an inner surface of the second cover plate 320 in proximity to the inner peripheral wall 324. The inner peripheral wall 324 and the outer peripheral wall 332 clamp therebetween the second front cover-engaging end portion 312 in proximity to the second end flange 3122.

A plurality of second interlocking units are provided on the second cover plate 320 and the second clamping ring 33 so as to interlock the second cover shell 32 and the second cushion ring 31, so that the second cover shell 32 covers one end of the passage 311. The second interlocking units include a plurality of angularly spaced-apart second engaging holes 337 provided in the second clamping ring 33, and a plurality of angularly spaced-apart second engaging hooks 321 provided on the second cover plate 320 to engage respectively the second engaging holes 337.

It should be noted that the passage 311 in the forehead abutment body 3 is used as a heat-dissipating passage for the user's forehead. The heat is discharged via the vent hole 314. The vent hole 314 also functions so that the first cushion ring 31 will not produce a suction force against the user's forehead which can cause discomfort to the user. Further, since the first cushion ring 11, the resilient forehead support 2, and the second cushion ring 31 are all made of silicone, they can be formed integrally as one body.

The adjustable head strap unit 4 is connected to the mask body 1 and the forehead abutment body 3 so as to secure the same to the user's head, and includes a main body 41 covering the back of the user's head, left and right lower straps 42 (see FIG. 10), left and right upper straps 43 (see FIG. 10), and a plurality of inter-engaging units 15 provided on the first cover plate 120 and the left and right lower straps 42. The inter-engaging units 15 include left and right rounded lug members 151 projecting outwardly and respectively from left and right sides of the first cover flange 124, and left and right hooking members 152 provided respectively on the left and right lower straps 42. Each of the left and right rounded lug members 151 has a neck section 153 projecting outwardly from an outer face of the first cover flange 124, and a ball-shaped head section 154 formed on one end of the neck section 153 that is distal from the first cover flange 124. Each of the left and right hooking members 152 includes a looped portion 156, and a substantially C-shaped hook portion 155 projecting outwardly from one end of the looped portion 156 to engage releasably the neck section 153 of the respective rounded lug member 151. The C-shaped hook portion 155 is prevented from moving out of the neck section 153 along an axial direction of the neck section 153 by the ball-shaped head section 154 of the respective rounded lug member 151.

Figure 2:
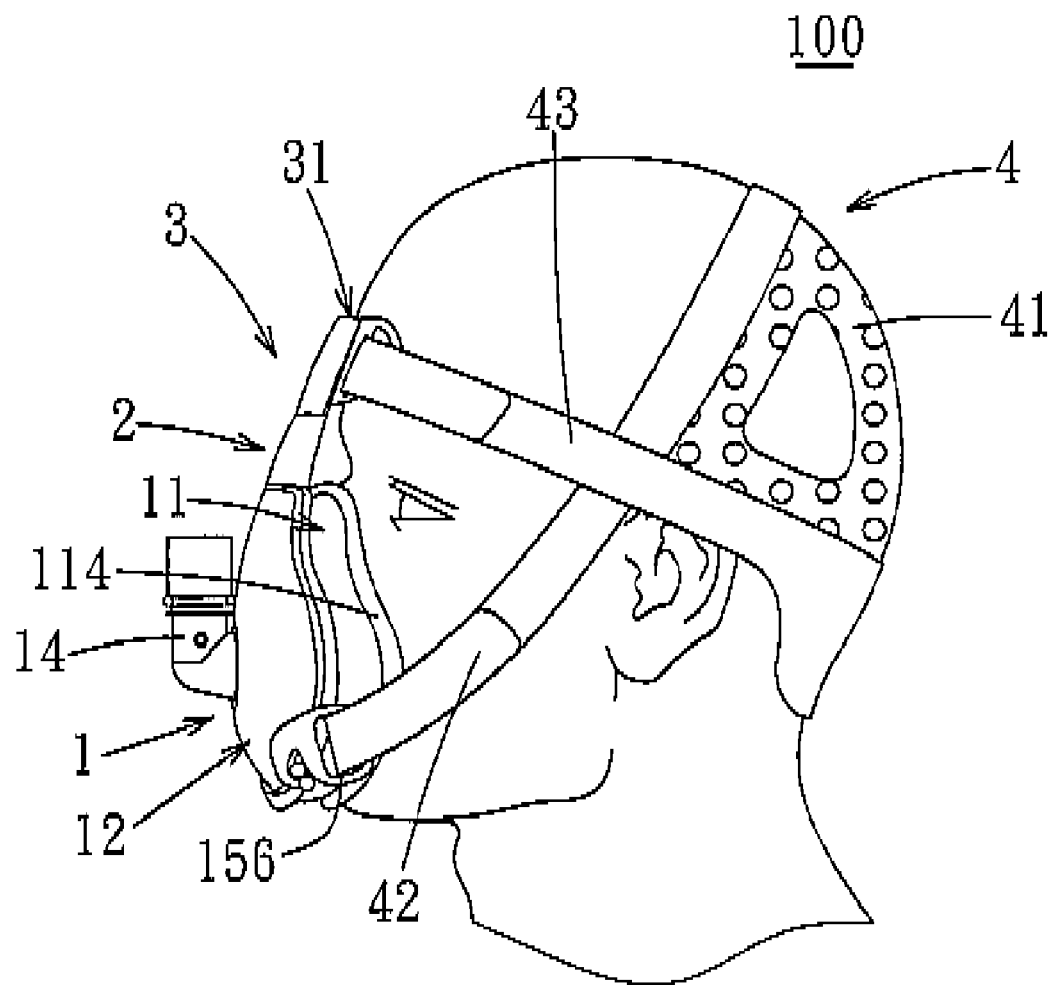
FIG. 2 is a perspective view of a respiratory mask according to the preferred embodiment of this invention in a state of use.

In this embodiment, the left and right lower straps 42 extend downwardly and respectively from left and right sides of the main body 41, and the left and right upper straps 43 extend forwardly and respectively from left and right sides of the main body 41, as best shown in FIG. 2. Each of the left and right lower straps 42 has an outer surface provided with a loop fastener 422, and a free end portion provided with a hook fastener 421. Similarly, each of the left and right upper straps 43 has an outer surface provided with a loop fastener 432, and a free end portion provided with a hook fastener 431. The free end portions of the left and right lower straps 42 are inserted through the looped portions 156 of the respective hooking members 152, and are folded back upon themselves so as to inter-engage releasably the hook and loop fasteners 421, 422 provided on the free end portions and the outer surfaces of the respective lower straps 42. The free end portions of the left and right upper straps 43 are inserted through the respective strap-engaging looped portions 322 of the second cover shell 3, and are folded back upon themselves so as to inter-engage releasably the hook and loop fasteners 431, 432 provided on the free end portions and the outer surfaces of the respective upper straps 43.

Figure 13:
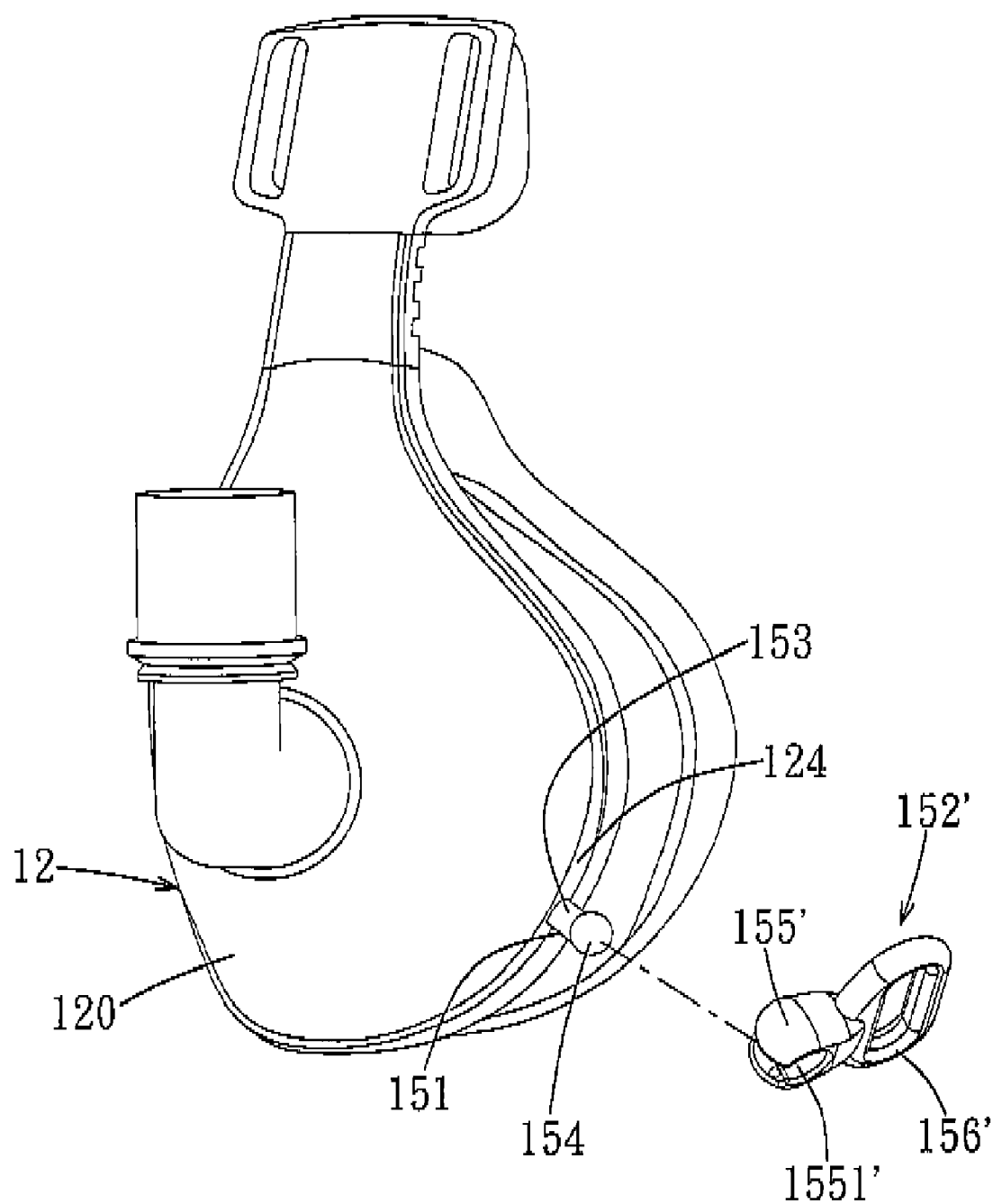
FIG. 13 illustrates an alternative form of a hooking member of the preferred embodiment.

In an alternative embodiment, as shown in FIG. 13, each of the left and right hooking members 152' (only the right hooking member 152' is shown in FIG. 13) may include a looped portion 156' to connect with the respective left or right lower strap 42 (see FIG. 2), and a substantially C-shaped clamp portion 155' projecting outwardly from the looped portion 156' and having an inner surface provided with a stepped surface 1551'. The C-shaped clamp portion 155' is engaged releasably to the respective rounded lug member 151 in such a manner that the ball-shaped head section 154 is engageable with the stepped surface 1551' and the C-shaped clamp portion 155' is rotatable relative to the ball-shaped head section 154, thereby permitting multi-directional movement of each hooking member 152' relative to the first cover shell 12.

The lengths of the upper and lower straps 43, 42 are adjustable as needed to correspond to the different facial dimensions of the users so as to produce suitable pulling forces against the mask body 1 and the forehead abutment body 3. Further, through the resilient bendable characteristics of the resilient forehead support 2, the first and second cushion rings 11, 31 can simultaneously and respectively abut against the user's nose and mouth and the user's forehead. Moreover, through the presence of the first and second annular contact faces 116, 115 in the first rear abutment end portion 114 of the first cushion ring 11, the mask body 1 provides for a double sealing effect and air leakage within the mask body 1 can be prevented. Hence, a continuous airflow with a definite pressure can flow into the airflow channel 111 through the air supply tube 14 and enter the user's airway through the user's nose, thereby effectively maintaining smooth flow of air in the user's airway.

Figure 11:
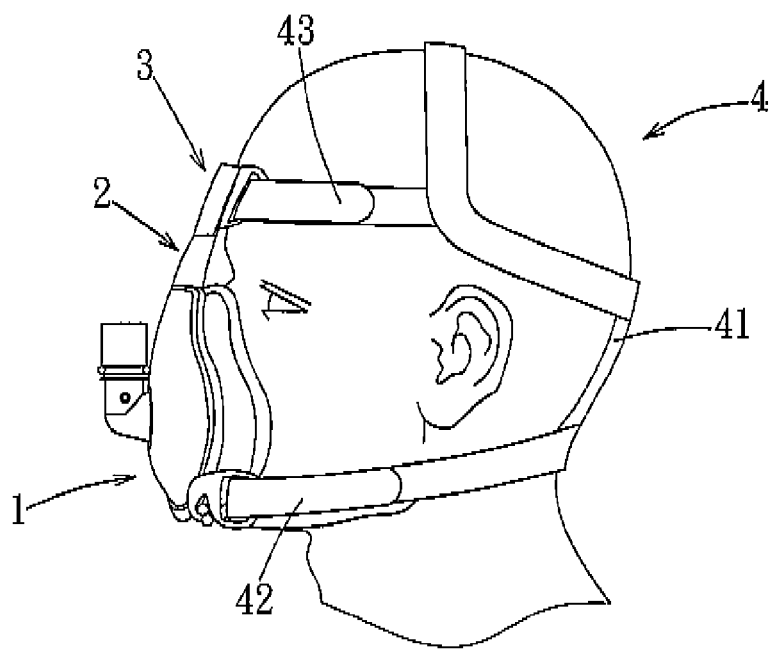
FIG. 11 illustrates an alternative form of the adjustable head strap unit.
Figure 12:
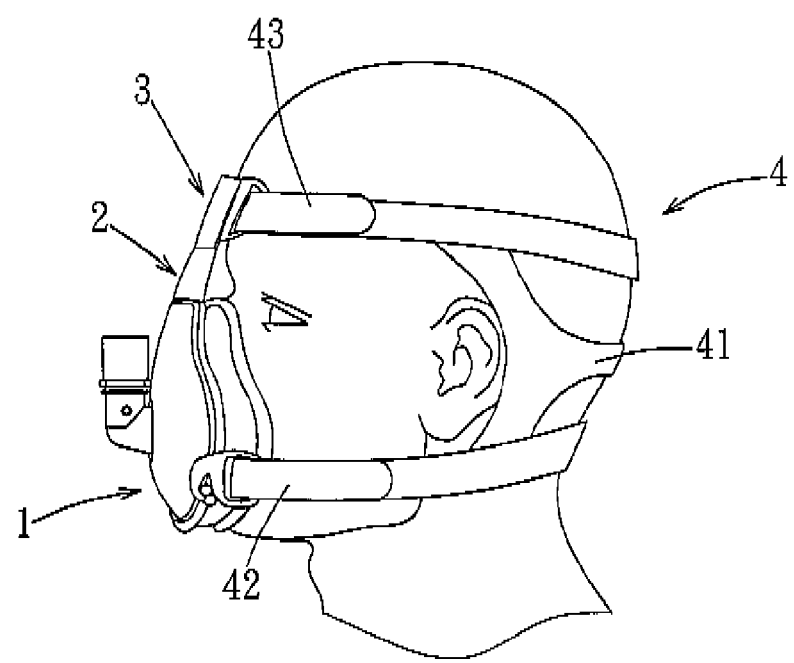
FIG. 12 illustrates another alternative form of the adjustable head strap unit.

The aforesaid hook and loop fasteners 421, 422, 431, 432 may be replaced by other structures, such as snaps, buttons, or the like, as long as the lengths of the upper and lower straps 43, 42 can be effectively adjusted. The main body 41 may be made of breathable material with heat-dissipating holes 411 (see FIG. 10), and may have different shapes, such as those shown in FIGS. 11 and 12. Further, the head strap unit 4 may include only the upper and lower straps 43, 42 so that the main body 41 may be dispensed herewith. As long as suitable pulling forces can be effected on the mask body 1 and the forehead abutment portion 3, any configuration of the head strap unit 1 is acceptable.

When the user desires to remove the respiratory mask 100 after adjusting the upper and lower straps 43, 42 so that the first and second cushion rings 11, 31 abut sealingly and respectively against the user's nose and mouth and the user's forehead, he or she simply disengages the hook portions 155 of the left and right hooking members 152 from the respective neck sections 153 of the left and right rounded lug members 151. To put on the respiratory mask 100, the hooking portions 155 of the left and right hooking members 152 are re-engaged to the respective neck sections 153 of the left and right rounded lug members 151. Hence, wear and removal of the respiratory mask 100 of the present invention are very simple and quick. The user can easily operate the respiratory mask 100 by himself/herself even in the middle of the night.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

We claim:

1. A respiratory mask comprising:
    a single-piece first cushion ring defining an airflow channel and having a first surrounding wall that extends around said airflow channel and that includes a first rear abutment end portion adapted to abut against a user's face below the forehead, and a first front cover-engaging end portion opposite to said first rear abutment end portion, said first front cover-engaging end portion having an inner surface provided with an annular first retaining recess extending around said airflow channel, and an annular first end flange projecting inwardly from an end of said first front cover-engaging end portion in proximity to said annular first retaining recess;
    a first cover shell having a first cover plate engaged to said first front cover-engaging end portion and provided with a connecting hole that is adapted to be connected to an air supply source;
    a resilient forehead support connected to a top end of said first front cover-engaging end portion and bendable toward said first rear abutment end portion;
    a resilient forehead abutment body connected to a top end of and supported by said resilient forehead support and including a second cushion ring adapted to abut against the forehead of the user; and
    an adjustable head strap unit connected to said first cover shell and said resilient forehead abutment body; and
    a first clamping ring fitted in said annular first retaining recess and having an inner peripheral wall that extends around said airflow channel and that has front and rear edges, an outer peripheral wall that extends around said inner peripheral wall, that abuts against said inner surface of said first front cover-engaging end portion, and that has front and rear edges, an annular groove formed between said inner and outer peripheral walls and opening at said front edges of said inner and outer peripheral walls, and a web portion interconnecting said rear edges of said inner and outer peripheral walls, said front edge of said outer peripheral wall abutting against said annular first end flange.

2. The respiratory mask of claim 1, wherein said resilient forehead support has a main body that includes a front planar wall, a plurality of substantially horizontal ribs projecting rearwardly from said front planar wall, horizontal valleys between said horizontal ribs, and a pair of lower engaging grooves formed in a bottom end of said main body, said first cover plate being further provided with a pair of upper engaging hooks engaged respectively to said lower engaging grooves.

3. The respiratory mask of claim 2, wherein said main body further includes a plurality of substantially vertical ribs disposed between said front planar wall and said horizontal ribs, and vertical valleys formed between said vertical ribs.

4. The respiratory mask of claim 1, wherein said resilient forehead support, said first cushion ring, and said second cushion ring are connected integrally to form one body.

5. The respiratory mask of claim 1, wherein said resilient forehead support is configured as a neck portion between said first cushion ring and said resilient forehead abutment body.

6. The respiratory mask of claim 1, wherein said resilient forehead support is made of silicone.

7. The respiratory mask of claim 1, wherein said first rear abutment end portion includes a first annular contact face adapted to contact the user's face, a first annular wall extending forwardly from an outer peripheral end of said first annular contact face toward said first front cover-engaging end portion, a second annular contact face surrounded by said first annular contact face and adapted to contact the user's face, and a second annular wall extending around said airflow channel, extending forwardly from an outer peripheral end of said second annular contact face toward said first front cover-engaging end portion, and surrounded by said first annular wall, said first and second annular walls being interconnected in proximity to said first front cover-engaging end portion.

8. The respiratory mask of claim 7, wherein said second annular contact face is softer than said first annular contact face.

9. The respiratory mask of claim 1, wherein said first cover plate has a first cover flange extending over and abutting against an outer surface of said first front cover-engaging end portion in proximity to said annular first end flange, said front edge of said outer peripheral wall clamping said annular first end flange against said first cover plate in proximity to said first cover flange, said first cover flange and said outer peripheral wall of said first clamping ring clamping therebetween said first front cover-engaging end portion in proximity to said annular first end flange.

10. The respiratory mask of claim 9, further comprising a plurality of first interlocking units provided on said first cover plate and said first clamping ring to interlock said first cover shell and said first cushion ring.

11. The respiratory mask of claim 10, wherein said first interlocking units include a plurality of angularly spaced-apart first engaging holes provided in said first clamping ring, and a plurality of angularly spaced-apart first engaging hooks provided on said first cover plate to engage respectively said first engaging holes.

12. The respiratory mask of claim 11, wherein said first engaging holes are formed between said inner and outer peripheral walls in proximity to said annular groove, and said first engaging hooks project rearwardly from an inner surface of said first cover plate into respective said first engaging holes and are spaced apart from said first cover flange.

13. The respiratory mask of claim 2, wherein said adjustable head strap unit includes left and right lower straps, and a plurality of inter-engaging units provided on said first cover plate and said left and right lower straps.

14. The respiratory mask of claim 13, wherein said inter-engaging units include left and right rounded lug members projecting outwardly and respectively from left and right sides of said first cover flange, and left and right hooking members provided respectively on said left and right lower straps to engage releasably and respectively said rounded lug members.

15. The respiratory mask of claim 14, wherein each of said left and right hooking members includes a looped portion to connect with a respective one of said left and right lower straps, and a hook portion projecting outwardly from said looped portion to engage releasably a respective said rounded lug member.

16. The respiratory mask of claim 14, wherein each of said left and right hooking members includes a looped portion to connect with a respective one of said left and right lower straps, and a substantially C-shaped clamp portion projecting outwardly from said looped portion to engage releasably a respective said rounded lug member, said C-shaped clamp portion having an inner surface provided with a stepped surface, each of said rounded lug members having a ball-shaped head section inserted releasably into said C-shaped clamp portion and engageable with said stepped surface.

17. The respiratory mask of claim 13, wherein said second cushion ring has a second rear abutment end portion adapted to abut against the forehead of the user and a second front cover-engaging end portion opposite to said second rear abutment end portion, said forehead abutment body further including a second cover shell connected to said second cushion ring, said head strap unit further including left and right upper straps, said second cover shell having left and right strap-engaging looped portions provided respectively on left and right sides of said second cover shell to connect respectively with said left and right upper straps.

18. The respiratory mask of claim 17, wherein said main body of said resilient forehead support further includes a pair of upper engaging grooves formed in a top end of said main body, said second cover plate further having a pair of lower engaging hooks engaged respectively to said upper engaging grooves.

\* \* \* \* \*